(12) United States Patent
Kumar

(10) Patent No.: US 6,545,240 B2
(45) Date of Patent: Apr. 8, 2003

(54) METAL SCRAP SORTING SYSTEM

(75) Inventor: Pradeep Kumar, Ann Arbor, MI (US)

(73) Assignee: Huron Valley Steel Corporation, Belleville, MI (US)

(*) Notice: Subject to any disclaimer, the term of this patent is extended or adjusted under 35 U.S.C. 154(b) by 0 days.

(21) Appl. No.: 09/882,887

(22) Filed: Jun. 15, 2001

(65) Prior Publication Data

US 2003/0034281 A1 Feb. 20, 2003

Related U.S. Application Data

(63) Continuation of application No. 09/491,737, filed on Jan. 27, 2000, now abandoned, which is a continuation of application No. 08/990,098, filed on Dec. 12, 1997, now abandoned, which is a continuation of application No. 08/602,618, filed on Feb. 16, 1996, now abandoned.

(51) Int. Cl.⁷ .............................. B07C 5/34; G01J 3/30
(52) U.S. Cl. ...................................... 209/579; 356/318
(58) Field of Search ................................. 356/318, 317; 209/579, 576, 685, 639

(56) References Cited

U.S. PATENT DOCUMENTS

| | | | | |
|---|---|---|---|---|
| 5,034,613 A | * | 7/1991 | Denk et al. | 356/318 |
| 5,042,947 A | * | 8/1991 | Potzschke et al. | 356/318 |
| 5,316,983 A | * | 5/1994 | Fujimori et al. | 437/250 |
| 5,381,224 A | * | 1/1995 | Dixon et al. | 356/72 |
| 5,628,410 A | * | 5/1997 | Smith et al. | 209/579 |
| 6,008,896 A | * | 12/1999 | Sabsabi et al. | 356/318 |
| 6,008,897 A | * | 12/1999 | Sabsabi et al. | 356/318 |
| 6,060,677 A | * | 5/2000 | Ulrichsen et al. | 209/577 |
| 6,366,353 B1 | * | 4/2002 | Brown et al. | 356/318 |
| 6,466,309 B1 | * | 10/2002 | Kossakovski et al. | 356/73 |

FOREIGN PATENT DOCUMENTS

| | | | | |
|---|---|---|---|---|
| CA | 2050608 A1 | * | 3/1992 | G01N/21/25 |
| DE | 4302283 A1 | * | 7/1994 | B07C/5/34 |
| DE | 4426475 A1 | * | 2/1995 | G01N/21/63 |
| DE | 4426490 A1 | * | 2/1995 | G01N/21/63 |
| EP | 231027 A | * | 8/1987 | G01N/21/47 |

OTHER PUBLICATIONS

Applied Spectroscopy, vol. 49, No. 4, 1995, p. 499–507, "Quantitative Analysis of Aluminum Alloys by Laser–Induced Breakdown Spectroscopy and Plasma Characterization", Mohamad Sabsabi and Paolo Cielo.*

* cited by examiner

Primary Examiner—Donald P. Walsh
Assistant Examiner—Daniel K Schlak
(74) Attorney, Agent, or Firm—Brooks & Kushman P.C.

(57) ABSTRACT

A system for sorting randomly positioned, irregularly shaped scrap metal particles on a moving conveyor employs laser-induced breakdown spectroscopy (LIBS), and includes an image detector for locating the particles as they path through a predefined viewing area, a position detector for detecting movement of the conveyor, a laser system for providing laser pulses, a scanner assembly for directing the pulses to selected locations within a target area, a light collector, a light distribution and spectral analyzer for isolating and measuring at least one selected band from the collected light, a separator, and suitable logic for identifying the particles, monitoring their position, monitoring the output of the laser and, operating the scanner assembly to direct the pulses to the identified particle. The spectral data is then analyzed, each particle is categorized, and thereafter sorted.

60 Claims, 8 Drawing Sheets

METAL SCRAP SORTING SYSTEM

This is a continuation of application Ser. No. 09/491,737, filed on Jan. 27, 2000, now abandoned, which is a continuation of application Ser. No. 08/990,098, filed on Dec. 12, 1997, now abandoned, which is a continuation of application Ser. No. 08/602,618, filed on Feb. 16, 1996, now abandoned.

TECHNICAL FIELD

This invention relates to a system and method for rapidly sorting irregularly shaped scrap metal particles randomly located on a moving conveyor based on the optical analysis of laser-induced plasmas.

BACKGROUND ART

The spectroscopy technique known as Laser-Induced Breakdown Spectroscopy (LIBS), Laser Spark Spectroscopy (LSS), or Laser-Induced Optical Emission Spectroscopy (LIOES) uses a focused laser beam to vaporize and subsequently produce spectral line emissions from a sample material. In this way samples placed at a distance from the analyzing instrumentation, can be analyzed for their chemical composition. It has been shown that a plurality of laser pulses increases the sensitivity of the technique for samples contaminated with paint, dirt, etc., on their surface. Since objects located at a distance could be analyzed rapidly, the method has also been recommended as a possible detection technique in the rapid sorting of mixed scrap metals (see "Analysis of Metals at a Distance Using Laser-Induced Breakdown Spectroscopy." D. A. Cremers—Appl. Spectroscopy 1987).

Attempts have been made to use laser-induced breakdown spectroscopy ("LIBS") to analyze metal particles to determine their composition in order to sort the particles. U.S. Pat. No. 5,042,947 discloses utilizing LIBS to sort metal particles. The '947 patent, however, requires the use of a randomly triggerable laser system, such as an excimer laser. Excimer lasers are generally more expensive and less industrially rugged compared to fixed frequency solid-state lasers such as Nd-YAG lasers.

The '947 patent also requires that the metal particles be conveyed into an inspection path where they will each individually pass a fixed inspection point upon which the pulsed laser beam is trained. This process, however, provides for no mechanical means for arranging the moving scrap metal particles in single file, or evenly spacing the particles in a manner expected by the fixed inspection and analysis instrumentation. Experience shows that it is difficult, if not impossible, to arrange and evenly space scrap particles in a high volume production environment. Even if this is possible, the speed of processing would be greatly limited by the speed of orienting each of the scrap particles into a single file so that each of the particles passes the fixed inspection point.

The '947 patent further requires irradiation of the surface of each particle with an initial cleaning pulse and subsequent removal of the plasma produced by the cleaning pulse using an air jet prior to the irradiation of the surface of the particle with an analyzing pulse. An air jet requires a finite time to initiate, and a rapidly moving particle would advance a certain distance during this time. Thus, it would be difficult, if not impossible, to direct more than one pulse to the same target spot of a selected particle. In general, because of the irregular shape of scrap metal particles, it would be difficult, if not impossible, to strike a particle on the same spot when the laser beam is redirected between pulses. Again, even if practically feasible, these additional processing steps would greatly reduce the speed of processing the scrap particles.

It is also known to sort objects located on a moving conveyor by periodically acquiring color images of the objects and discriminating between the objects on the basis of their color. While this method may be employed for sorting certain metal scrap, such as, for example, sorting copper from aluminum, image processing-based color sorting systems are ineffective for sorting randomly oriented scrap metal particles of similar colors, such as aluminum and magnesium, or different aluminum alloys.

It is particularly desirable to efficiently separate scrap into alloy families, since mixed scrap of the same alloy family is worth much more than that of indiscriminately mixed alloys. For example, in the blending methods used to recycle aluminum, any quantity of scrap comprised of similar alloys and of consistent quality, has more value than scrap consisting of mixed aluminum alloys.

DISCLOSURE OF THE INVENTION

One object of the present invention is to provide a system for sorting irregularly shaped scrap metal particles based upon the optical analysis of laser-induced plasmas, as the particles are rapidly transported in random locations on a conveyor.

Another object of the present invention is to provide a system which is capable of rapidly sorting metal scrap particles, such as different aluminum alloy families, which may not be easily differentiated from each other by their color.

Another object of the present invention to provide a LIBS metal scrap sorting system including a scanner system which provides focused laser pulses having uniform power densities along a plane located at the surface of the conveyor.

Another object of the present invention is to provide a LIBS metal scrap sorting system including image detection and processing arrangement that could be used to provide information about a plurality of particles randomly located on a conveyor belt, including location, size, and shape of each particle, to a sorting control system.

Another object of the present invention is to provide a LIBS metal scrap sorting system including an illumination system for image detection that provides uniform controlled illumination of the scrap pieces from a plurality of directions so that the image detected is an actual two-dimensional outline of the particle and is not influenced by the combined effects of particle shape, surface reflectivity, and the geometry of the illumination system.

Another object of the present invention is to provide a LIBS metal scrap sorting system including a fixed frequency laser system configured so as to frequently provide multiple laser pulses during an extremely small interval of time so that all the pulses could be directed to a randomly located scrap particle using a single positioning movement of a laser beam scanner.

In carrying out the above and other objects, the scrap sorting system of the present invention includes a conveyor for conveying the randomly shaped scrap metal particles in a random orientation, an image detector for electronically recording the image of a predefined viewing area through which the scrap particles are conveyed by the conveyor, a position detector for detecting movement of the conveyor, a laser system configured to provide a laser beam including a stream of a plurality of laser pulses within a selected time interval, and at least one laser scanner assembly including a positionable beam deflector to direct the laser pulses at a selected particle at any location in a selected target region on the conveyor and a focusing element mounted downstream of the source of the laser pulses from the beam deflector to focus the beam and provide uniform laser power density along a plane. The system further includes a light collector for collecting light from plasma produced from the particles as they are irradiated by the laser pulses, a light distribution and spectral analyzer system for isolating and measuring at least one selected band from the collected light, a separator to divert particles to different bins based on discriminator signals, and control logic for continuously acquiring an image of the selected viewing area of the conveyor, processing the image to identify and locate the scrap particles as they pass through the viewing area, monitoring the laser system to determine when the next laser pulses will be available, selecting a downstream location on the conveyor at which the next available stream of pulses of radiation may be directed at an identified particle, operating the scanner assemblies as required to direct the pulses at the selected target location, analyzing spectral data collected from the plasma, generating a discriminator signal based at least in part upon the spectral data analysis, and selectably activating the separator as a function of the discriminator signal to sort the analyzed particles.

In one embodiment, the laser beam is positionable both in the direction of travel of the conveyor as well as transverse to the direction of conveyance (i.e. across the width of the conveyor), so that a downstream location can be selected for irradiating each particle regardless of that particle's location on the moving conveyor. A target scanner assembly comprising one or more beam deflectors are utilized, each capable of directing multiple laser pulses when available to a selected point within a target area on the conveyor in time to ablate a scrap particle as it passes that point in the scanner's target area. The beam deflectors preferably comprise one or more galvanometric scanners including positionable mirrors for controllably directing the laser beams.

It will be appreciated that enough target scanner assemblies are employed so that the combined target areas of each of the scanner assemblies covers the entire width of the conveyor belt. In addition, some overlap of the target areas in the direction of the width of the belt may be desirable, for example, in an orientation where the target area of one scanner assembly is located downstream in the direction of travel of the conveyor but overlapping another target area in the direction of the width of the conveyor, so that alternative target points are available for a particular identified piece of scrap. This overlapping coverage of the conveyor using multiple scanner assemblies could provide for faster processing of the particles, either by allowing for a higher density of particles on the conveyor, or for processing at a higher conveyor speed.

In one embodiment, the system employs a laser system including two solid-state, fixed frequency lasers. It is desirable to provide a plurality of pulses to a selected target point within a period sufficiently short enough to allow for each of the laser pulses to strike and ablate a selected scrap particle at the same spot as it is being conveyed past that target point. Thus, for example, on a conveyor that is moving at approximately 300 feet per minute, the desired number of pulses must be fired and directed to the target point to strike the particle within a period of approximately 250 microseconds. For this time period, the movement (approximately 0.38 millimeters) of the scrap particle can be ignored considering the spot size of the laser beam, and the particle may be ablated with multiple pulses without operating the scanner assembly to redirect the laser beam between pulses.

In the preferred embodiment, up to four pulses may be directed on a target within 150 microseconds using two constant repetition rate Nd-YAG lasers operated in "double pulse" mode. In the double-pulse mode, the laser is Q-switched twice during a flashlamp cycle, resulting in two pulses separated by an extremely small time period (approximately 1–200 microseconds). Since particle movement during this time period is negligible, all four shots could be directed to the same spot using a single positioning of the scanner.

In yet another embodiment, a plurality of laser systems are provided, with each system capable of providing the desired plurality of pulses within a time interval sufficiently short to ablate a target point on a selected particle without repositioning the scanners between pulses. It will be appreciated that, by pooling a plurality of laser systems, the number of particles that can be sorted per second is not dependent upon the frequency of generation of the pulse stream from any single laser system.

An image detector, preferably including a conventional linescan camera, is located upstream from the scanner target area(s) to continually acquire images of a suitably illuminated image viewing area, and to determine the existence and location of scrap particles on the moving conveyor. The image detector also preferably includes a lighting system to provide controlled, uniform illumination of the viewing area.

A light collector, preferably comprising a plurality of optical fibers, is mounted to receive light from the generated plasma in the target area(s). A light distribution and spectral analyzer system is also provided for isolating and measuring at least one selected band from the light collected by the optical fibers.

The light distribution and spectral analyzer system includes at least one spectral filter, preferably in the form of a monochromater for isolating a selected band from the collected light, and a detector associated with each monochromater for generating a signal corresponding to the intensity of the selected band.

A system control, preferably in the form of one or more suitably programmed computers, monitors and manages collection of system data, including conveyor belt position data received from the position detector, image data received from the camera, laser pulse availability, and spectral emission data received from the light distribution and spectral analyzer system, and processes the data to control all of the major components of the system.

The system control also includes image processing logic for detecting the presence and location of the scrap particles, and may include additional known image processing capabilities, such as known shape and color information extraction algorithms, which may be utilized for sorting the scrap particles. Once identified, the linear advancement of these particles on the conveyor belt is monitored by the control system based on belt position data supplied by an encoder. When the control system determines that the next laser pulse stream will become available at a predetermined time in the future, the system identifies a particle in a target area. The scanner mirrors of the appropriate scanner assembly are positioned to deflect the pulse stream to a position expected to be occupied by the particle when the laser pulses become available.

The system control also includes data acquisition logic suitable for acquiring data from the various input hardware components, decision logic such as neural networks capable of classifying each of the scrap particles as one of a preselected list of alloy families based on the analysis of spectral and other data, output control logic for control of output hardware, and networking logic for the interconnection and the seamless operation of the various computer systems.

The system of the present invention thus effectively sorts randomly shaped and randomly located scrap metal particles, based on their chemical composition as they are conveyed on a high speed conveyor.

These and other objects, features, and advantages of the present invention are readily apparent from the following detailed description of the best mode for carrying out the invention when taken in connection with the accompanying drawings.

BEST MODE FOR CARRYING OUT THE INVENTION

Figure 1:
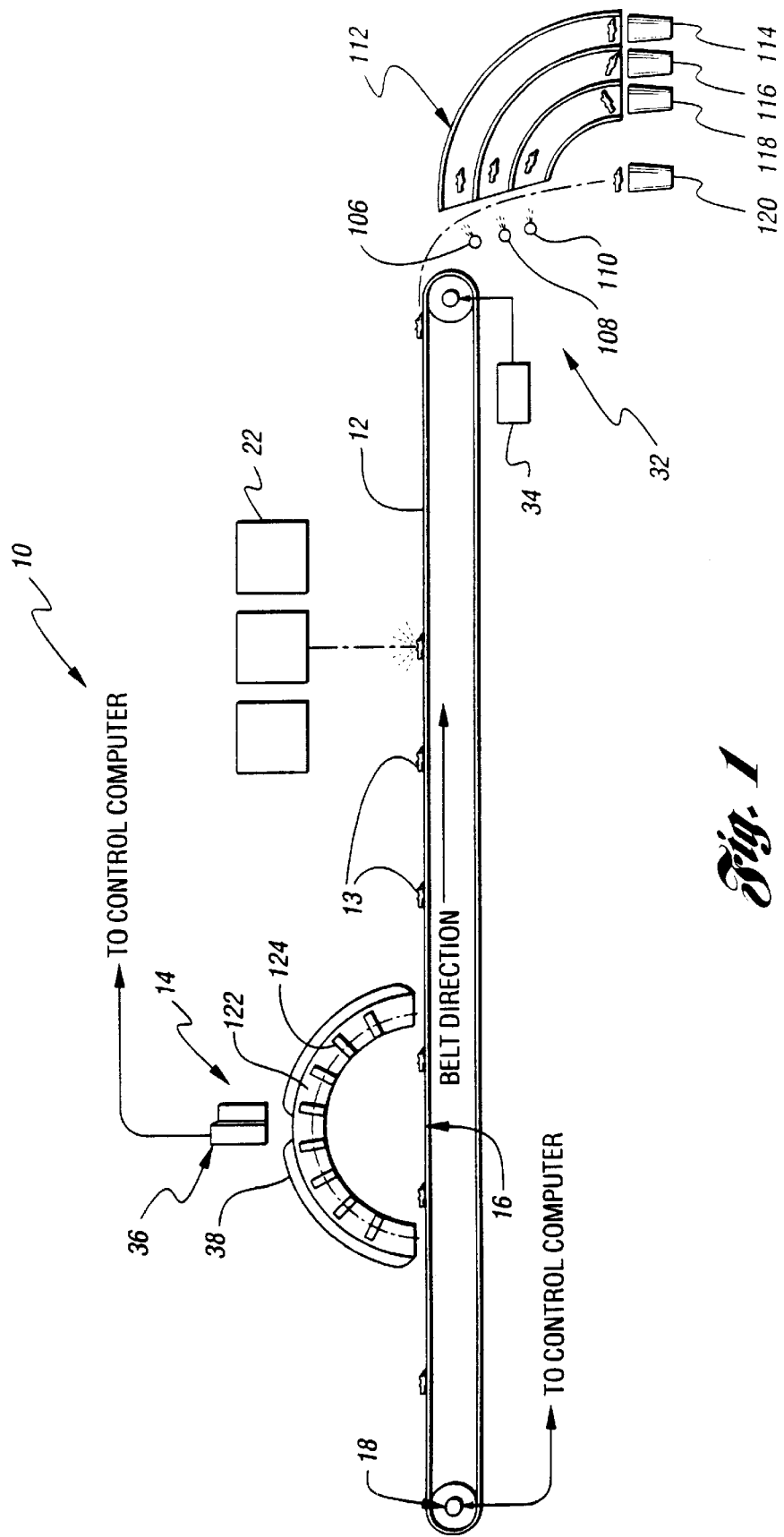
FIG. 1 is a diagrammatic side view of the sorting system of the present invention.
Figure 2:
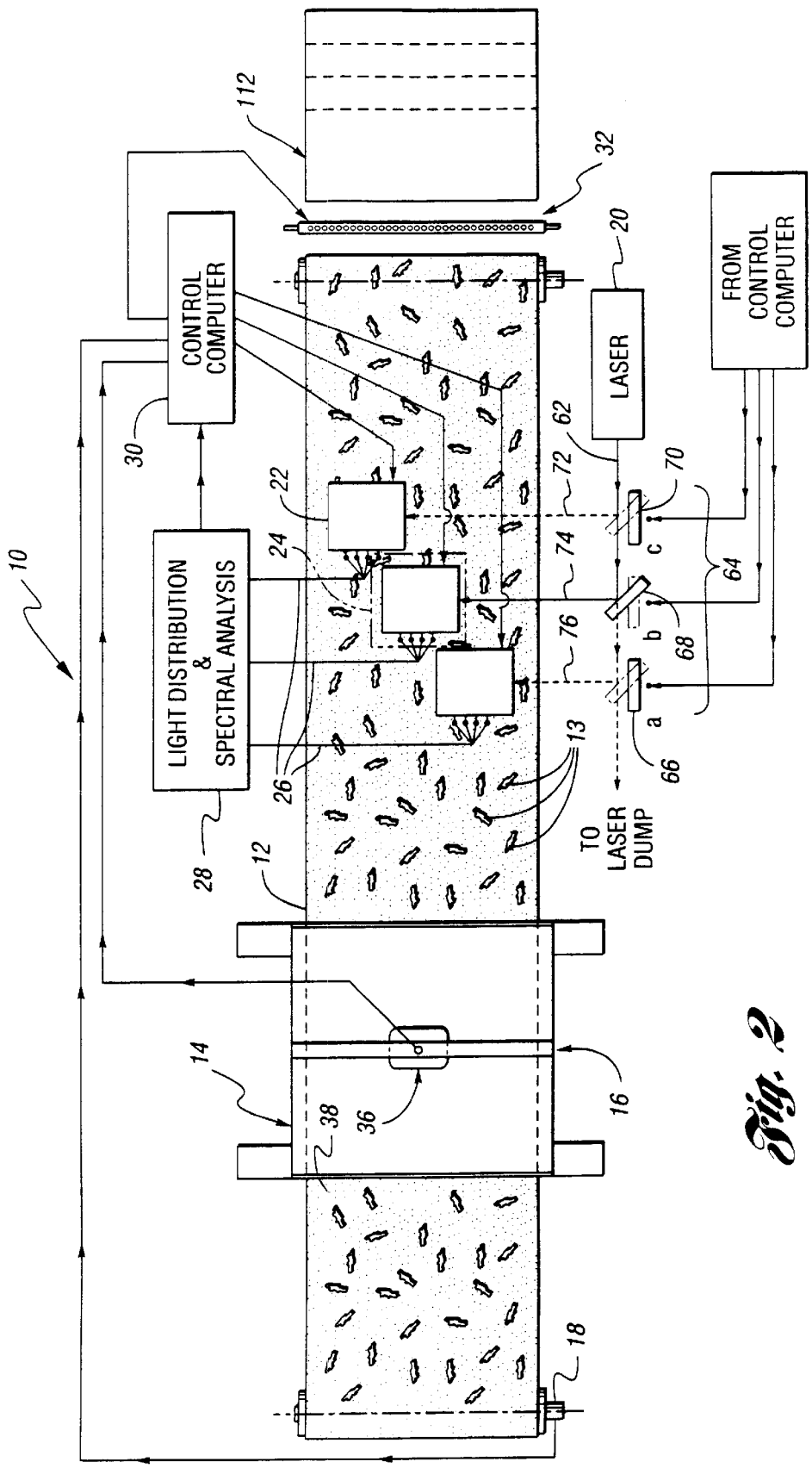
FIG. 2 is a diagrammatic top view illustrating an embodiment of the sorting system of the present invention.

Referring to FIGS. 1 and 2, the scrap metal sorting system 10 of the present invention employs a conveyor 12 for conveying randomly oriented and positioned scrap particles 13 along a linear path, an image detector 14 for continuously acquiring images of a predefined viewing area 16 above the moving conveyor, a position detector 18 for detecting movement of the conveyor, a laser system 20 employing at least one laser for providing a plurality of laser beam pulses within a preselected time interval, and a target scanner assembly 22 comprising at least one beam deflector for directing and focusing laser beam pulses available at constant intervals from the laser system to selected positions at uniform power densities along a plane within a target area 24 on the conveyor belt. The preselected time interval is chosen to be short enough to ablate a selected target spot on a detected scrap particle which has been conveyed to that location with multiple pulses without repositioning the scanner.

The system 10 further includes light collectors 26 comprising a plurality of optical fibers distributed to collect light from the generated plasma, and a light distribution and spectral analyzer unit 28 for the isolation and measurement of selected spectral components of the collected light.

A control 30 is provided for supervising and controlling the timing and operation of each of the components of the system to detect the presence of scrap particles, track their position downstream on the conveyor, direct a suitable number of laser pulses to that position at the appropriate time to ablate the detected particle, analyze the plasma produced from the irradiated particle, generate a discriminator signal based upon the analysis of the plasma, and selectively activate the separator as a function of the discriminator signal.

The system 10 further includes a separator 32 which may be selectively activated to direct the scrap particles along different paths as they reach the end of the conveyor, thereby sorting the particles in response to the image and spectral analysis information developed by the system.

The conveyor 12 is preferably a conventional endless belt conveyor employing a conventional drive motor 34 suitable to move the conveyor at speeds of 200 to 400 feet per minute. The position detector 18 is preferably a conventional encoder, operatively connected to the conveyor and the control 30 to provide continuous information corresponding to the movement of the conveyor belt.

The image detector 14 typically comprises a camera 36 and a lighting system 38. The camera 36 is trained upon a selected viewing area 16 of the conveyor 12 which is illuminated by the lighting system 38 for providing constant, controlled, uniform illumination of that viewing area. The camera 36 is preferably a linescan camera which provides digital image data corresponding to the viewing area to the control 30 with sufficient frequency such that the continuous images of the viewing area 16 provide an uninterrupted view of the surface of the moving conveyor. In one embodiment, this is accomplished by triggering the linescan camera to acquire an image at each pulse of the position encoder, so that acquisition of the images is linked directly to the movement of the conveyor. Thus, in this embodiment, the viewing area is a rectangle equal in its major dimension to the width of the belt and in its minor dimension to the distance moved by the conveyor belt during one encoder pulse (approximately 1 millimeter), thereby producing a "linescan" of the belt. Wider area scan cameras may also be used in place of the linescan camera of the preferred embodiment by suitably modifying the frequency of image acquisition, so long as the entire surface of the moving belt is scanned, and so long as the lighting system is modified to provide uniform multidirectional illumination of the enlarged viewing area.

The system control may be configured using general purpose high speed processors such as Pentium, Power PC, Alpha AxP, etc., which are commercially available, suitably programmed to perform all of the major processing functions described herein. The systems must be preferably interconnected using high speed networking schemes. The operating system is preferably the "QNX" real-time operating system. However, other operating software capable of distributed processing, as well as real time multi-tasking, may be used.

The system control 30 further includes hardware and electronic components necessary for the acquisition of data, as well as the control of electromechanical components. These may include high speed analog-to-digital converters or other suitable interfacing components for acquisition of data from one or more light detectors such as photomultiplier tubes, discrete signal input electronics for the acquisition of encoder signals as well as for the acquisition of synchronization signals indicating the availability of the next laser pulse stream, frame grabbers or other suitable interfacing components for the acquisition of image detector data, digital, analog, and/or discrete signal output electronics for the control of various scanners, as well as for the control of air jets incorporated in the separator, networking hardware for interconnection of the computer systems, and any other input and output hardware needed for acquisition of external signals, the control of any electromechanical components, and the networking and seamless operation of a plurality of computer systems.

Figure 3:
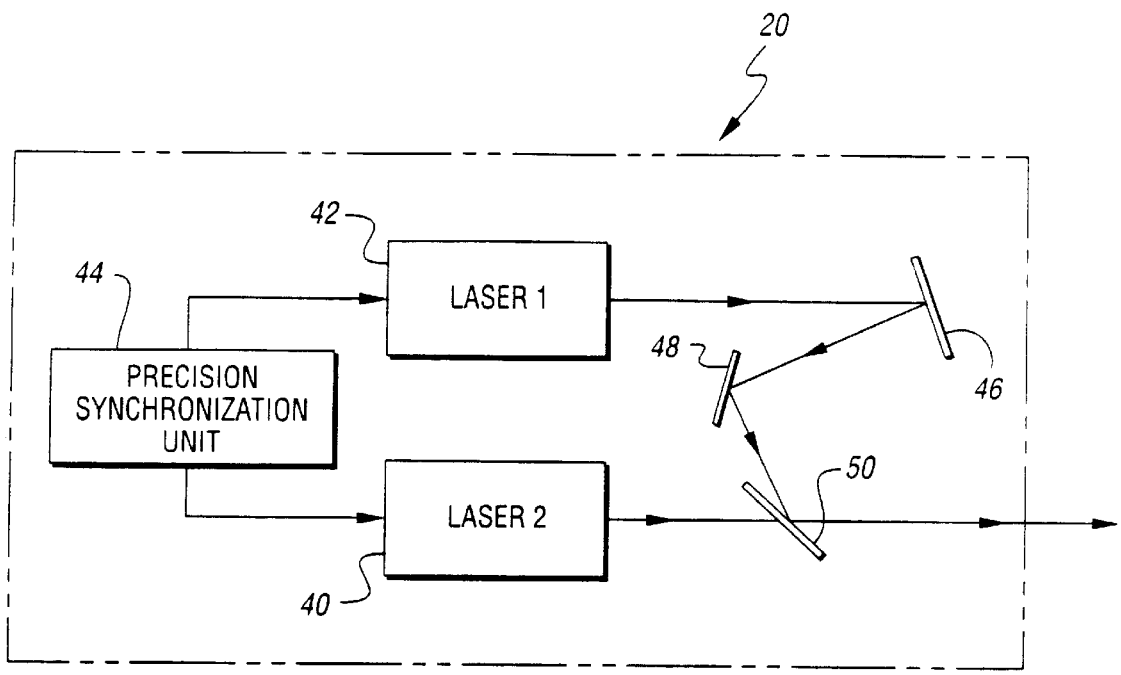
FIG. 3 is a diagram of the laser system of FIG. 2 employing a pair of synchronized lasers.

The laser system 20 employs one or more lasers suitable to provide a plurality of pulses sufficiently rapidly that the target scrap particle is ablated by each of the pulses without the need to re-position the scanner. Referring to FIG. 3, one embodiment of the present invention employs a pair of solid-state fixed frequency pulsed Q-switched Neodymium-yttrium aluminum garnet (commnonly known as Nd-YAG) lasers 40–42, a synchronizing unit 44, a pair of mirrors 46–48, and a polarizing beam splitter 50 for combining suitably polarized pulse streams from each of lasers 40 and 42 into a single selected path. The laser pulses may then be redirected as needed to a selected target point on the conveyor to ablate a scrap particle as it passes that target point. Each of the lasers 40–42 is operated in "double pulse" mode which produces two pulses separated by 1–200 microseconds and preferably about 50 microseconds. Thus, properly timed, the laser system 20 may provide four pulses fired over a period of 150 microseconds. Generated within this time interval, the movement of the scrap particle on the conveyor during this 150 microsecond time period would be negligible. As such, all four pulses could be directed to the same spot using a single scanner position. It should be noted that all of the components of the embodiment of the laser system 20 shown in FIG. 3 are available as Model "Surelite II-PIV," from Continuum Corporation, Santa Clara, Calif., U.S.A.

It should be noted that, while it is possible to operate solid-state lasers such as Nd-YAG at a variable rate, such operations produce non-uniform thermal conditions on the laser system with the result that the characteristics of the pulses produced would vary in their energy, duration, and spatial and temporal profile. These variations would result in non-uniform power densities for ablation and widely varying characterizations on the part of the plasma generated as a result of ablation making accurate determination of the composition of the particle difficult. Hence, it is preferred that these lasers be operated in a fixed frequency mode so as to generate pulses of predictable characterizations. Other comparable fixed frequency lasers may alternatively be utilized, so long as one or more of the lasers may be configured to provide multiple pulses within a short enough time span that the pulses can ablate a selected scrap particle at a selected target point without repositioning the scanner.

Figure 4:
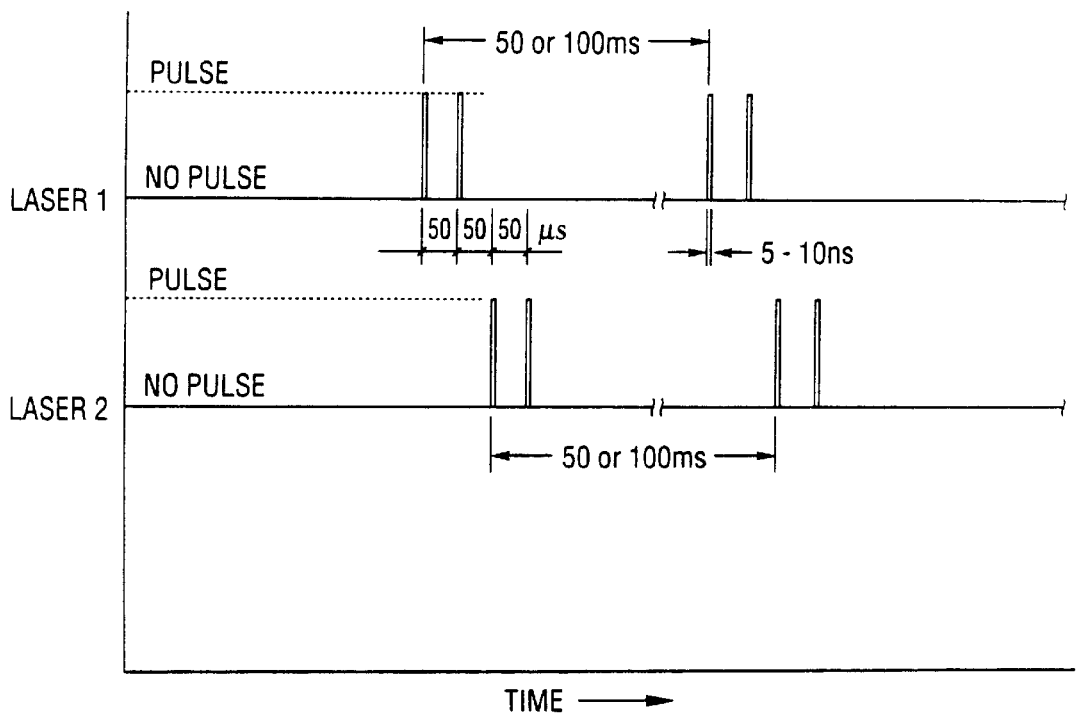
FIG. 4 is a timing diagram for the laser system of FIG. 3 when it is operated in the "double pulse" mode.

FIG. 4 illustrates a timing diagram for the two-laser system of FIG. 3 operating in "double pulse" mode. By synchronizing and coupling the output of each of the lasers, four pulses may be obtained within 150 microseconds, thereby providing the capability of directing multiple pulses at a selected spot on a moving scrap particle before the scanner has to be repositioned. These lasers may then be called upon again (in either 50 or 100 milliseconds based upon the basic operating frequency of the lasers) to supply another group of four pulses at about 50 microsecond intervals. It will be appreciated that additional laser systems may be utilized to selectively provide multiple pulses to ablate scrap particles at a greater frequency. Thus, for example, a pool of two laser systems, each with the capability illustrated in FIG. 4, may be utilized to supply groups of four pulses for each target scrap particle as frequently as about every 25 milliseconds.

Figure 5A:
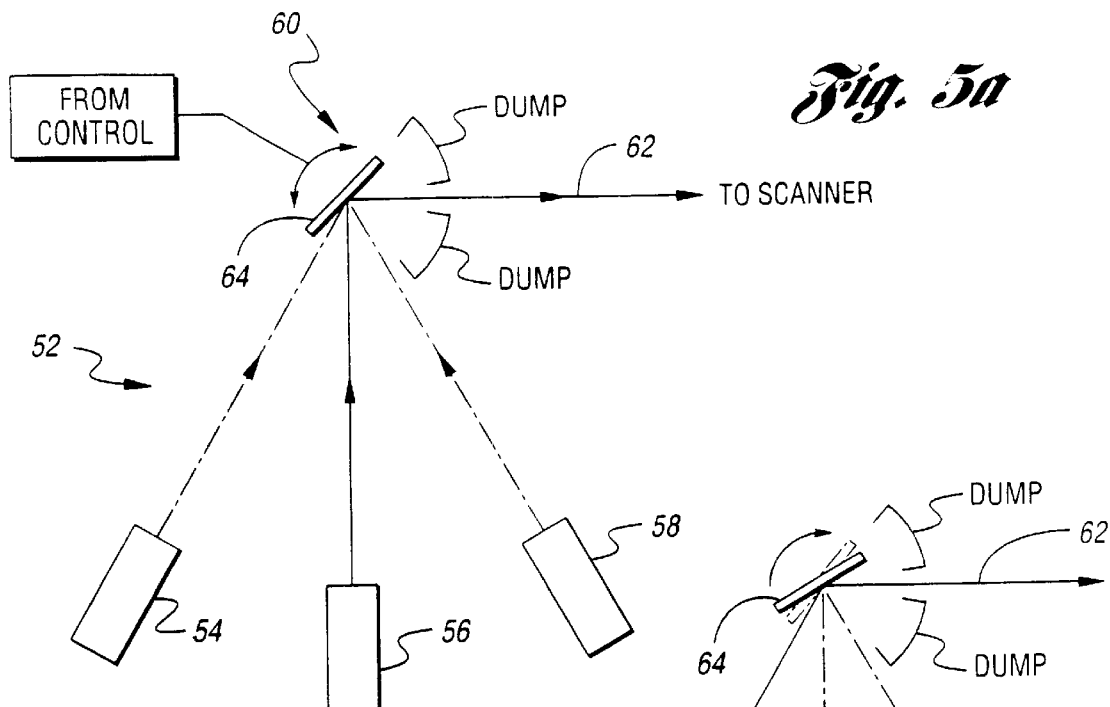
FIGS. 5a–5c are diagrammatic illustrations of a laser pool including three laser systems which may be utilized in an embodiment of the present invention.
Figure 5B:
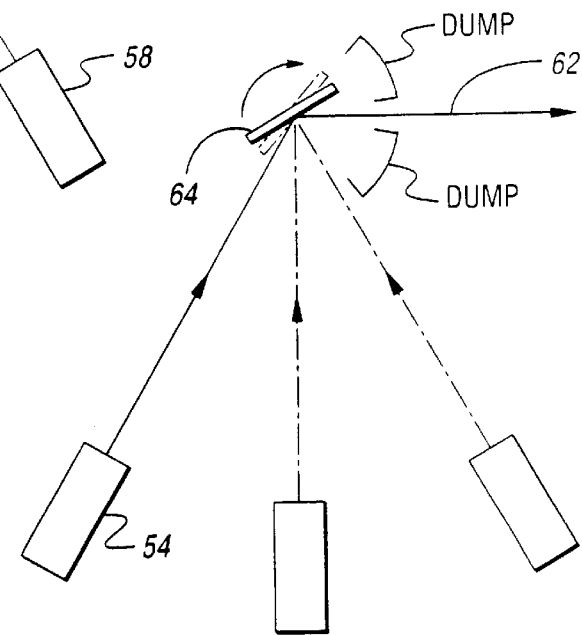
Figure 5C:
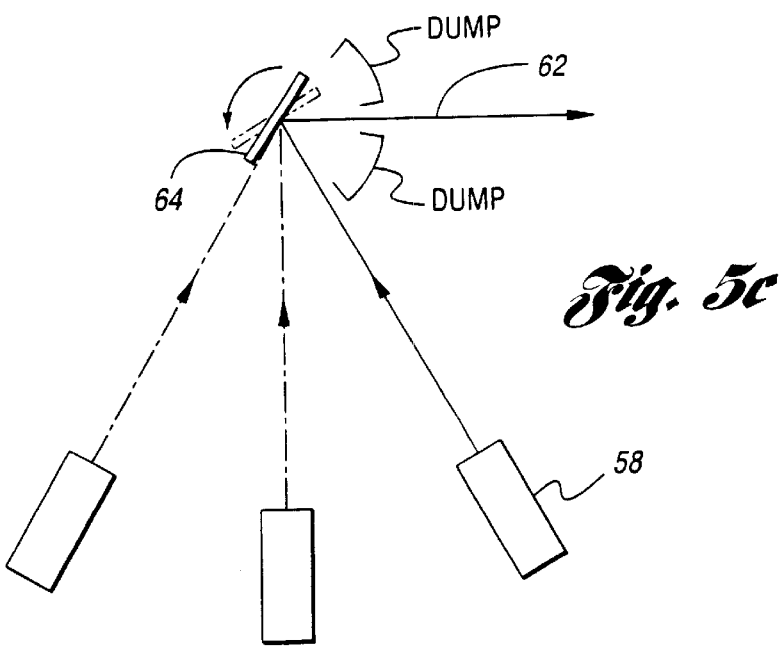

Referring now to FIGS. 5a–5c, one such multiple laser system embodiment employs a laser pool 52 including a plurality of laser systems 54, 56, 58 and a laser pool scanner assembly 60 which are under common control to direct multiple laser pulses, as required, along path 62 to one or more of the target scanner assemblies 22 in the system 10. The laser pool scanner assembly 60 includes a beam deflector 64 which preferably comprises at least one scanner with a positionable mirror. It will be appreciated that each of the laser systems 54–58 may be configured as shown in FIG. 3. Alternatively, each may contain one or more lasers capable of providing multiple pulses within a time interval suitable for ablating a moving scrap particle at a selected target position without repositioning the pool scanner mirror(s) 64, and without repositioning the mirror(s) in the target scanner assemblies 20 to which the laser pulses are directed.

FIG. 5a schematically illustrates the position of mirror 64 to direct multiple laser pulses from laser system 56 along a fixed path 62 to any one of the scanner assemblies 22 in the system 10. If a subsequent set of laser pulses is required sooner than the pulses can be supplied by laser system 56, mirror 64 is repositioned, as shown in FIG. 5b, to direct a set of multiple pulses from laser system 54 along the same fixed path 62 to one of the scanner assemblies 22. Similarly, if yet another set of laser pulses is subsequently required before either of laser systems 56 or 54 may again be utilized, scanning mirror 64 may again be repositioned, as shown in FIG. 5c, to direct multiple pulses from laser system 58 along the fixed path 62 to one of the scanner assemblies 22.

It will be appreciated that by providing a pool of laser systems, the frequency of supply of sets of laser pulses to the scanner assemblies 22 can be increased beyond the frequency rate of a single multiple-pulse set laser system. Similarly, by providing one or more scanning mirrors 64 to direct pulses from one of the selected laser systems 54–58 along a fixed path 62, pulses from any of the laser systems in the pool may be directed to any of the target scanners 22 as required.

In one embodiment, an intermediate scanner assembly 64 (shown in FIG. 2) including a plurality of beam deflectors, 66, 68, 70 preferably comprising positionable galvanometric scanners with mirror, is employed to direct the laser pulses from their source(s) directed along path 62 to the required target scanner assembly 22 as required. Control logic is provided to operate the galvanometric scanners to rotate the mirrors of the intermediate scanner assembly from a non-interfering position (such as indicated by the position of mirrors 66 and 70 in FIG. 2) to one or more operable positions (such as that shown by mirror 68 in FIG. 2) to direct a set of laser pulses from path 62 along a new path to one of the target scanner assemblies 22. In the example illustrated in FIG. 2, the pulses from a single laser system 20 are directed along path 62 to scanning mirror 68 in the intermediate scanner assembly 64, where the pulses are re-directed along path 74 to one of the target scanner assemblies 22. As shown, during the times when no pulses are required by the system, the fixed frequency lasers transmit the pulses along path 62 to a laser dump. As previously explained, laser system 20 could be replaced with a laser pool (such as laser pool 52 shown in FIGS. 5(a)–5(c)) which employ pool scanner assemblies 60 to direct laser pulses from one of the selected laser systems 54–58 in the laser pool 52 along path 62, where the pulses may be selectively rerouted to the target scanner assemblies 22 using intermediate scanner assembly 64.

Figure 6:
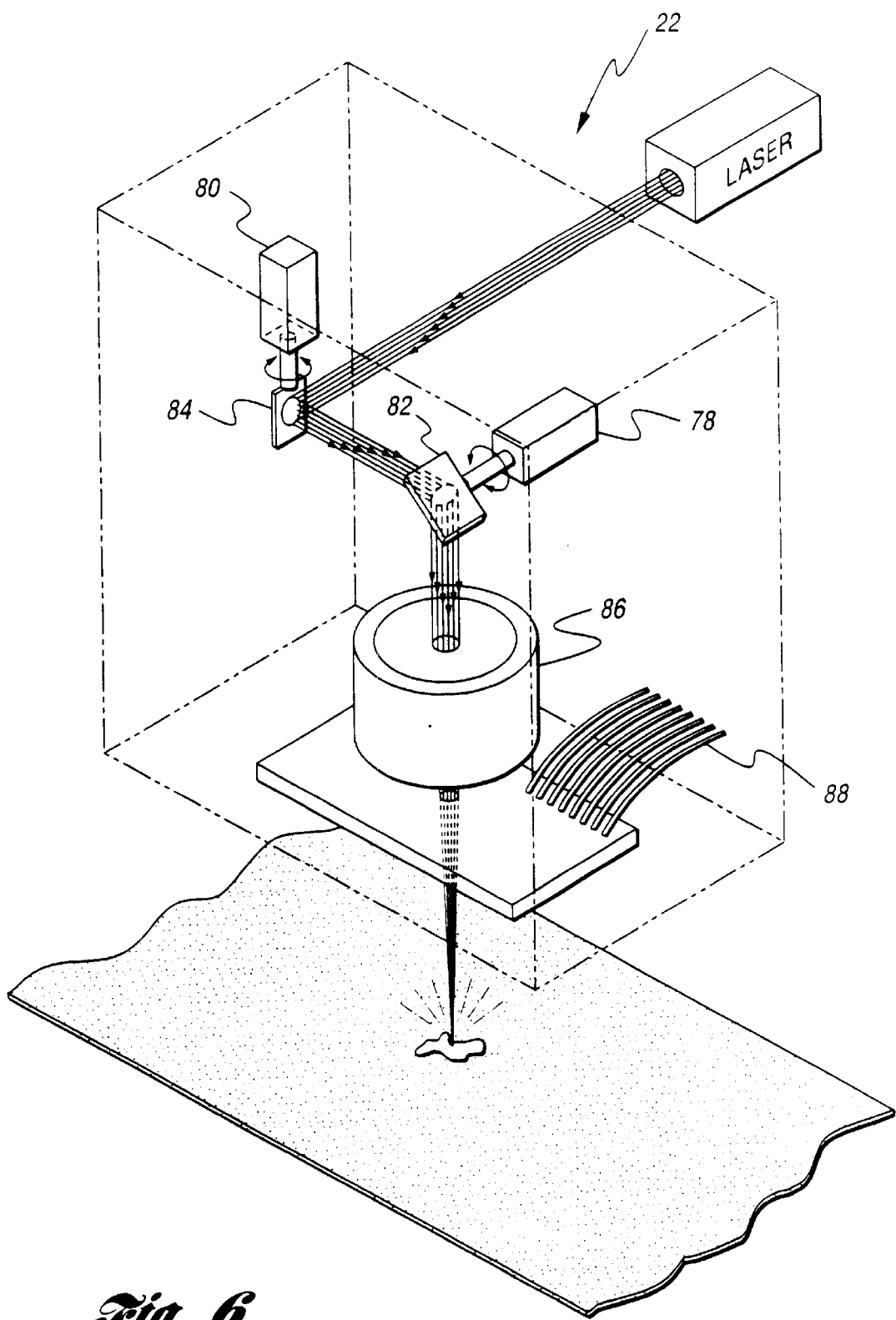
FIG. 6 is a diagram of one of the scanner systems shown in FIG. 2.

Referring now to FIG. 6, each of the target scanner assemblies 22 employ beam deflectors, also preferably in the form of positionable galvanometric scanners 78, 80 which position mirrors 82, 84 to direct laser pulses input to the target scanner assemblies 22 (such as via paths 72, 74, or 76 shown in FIG. 2) to a selected location within a target area covered by the target scanner assemblies 22 in time to ablate a selected scrap particle as it moves through the target area. The scanner assembly 22 also includes a focusing element 86, such as a lens, located downstream in the path of the laser pulses from the mirrors 82, 84 to focus the laser pulses. With this arrangement, as the scanners 78, 80 are operated to deflect the mirrors 82, 84 along their respective axes, the focal point of the pulses moves along a plane. This provides uniform power densities along a plane, such as the surface of the conveyor belt 12.

Figure 7B:
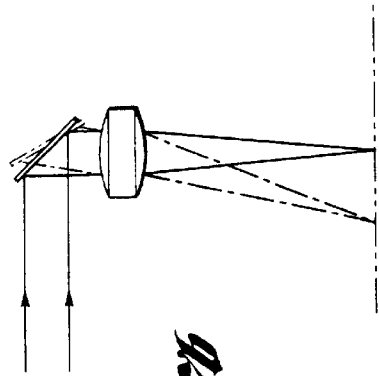
FIG. 7b is an illustration of a pre-optical scanner employed by the present invention.
Figure 7A:
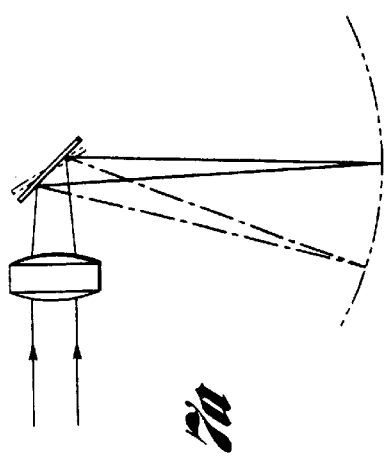
FIG. 7a is a graphic illustration of a post-optical scanner.

The advantage of the pre-lens scanning arrangement preferably employed in the present invention is schematically illustrated in FIGS. 7a and 7b. FIG. 7a illustrates a post-lens arrangement of a scanning mirror. This post-lens arrangement may be of relatively simple design, but results in the laser power density being uniform along an arc, and hence non-uniform on a plane such as that of the surface of the conveyor belt. With this arrangement, there is a depth-of-focus problem for a wide scan of targets on the conveyor. Non-uniform laser power densities result in more widely varying plasma conditions at different locations on the belt. These varying conditions would require more complex analysis algorithms to insure that the spectral data was useful in the sorting analysis and greatly reduce the accuracy and effectiveness of the spectral analysis, and many of the advantages gained from using solid-state lasers at fixed frequencies would be lost. In contrast, as shown in FIG. 7b, the pre-lens scanner mirror arrangement employed in the present invention, provides for uniform power density along a plane. If the optics are selected to provide the focal plane at about the surface of the conveyor belt, it will be appreciated that particles which are randomly located within the target area of a scanner assembly 22 could be provided with generally uniform laser power densities for ablation, resulting in a greater accuracy in sorting.

In addition, the focusing element is preferably a lens designed with a distortion characteristic that makes the image distance proportional to the field angle so that the scan is linear with the angular displacement of the scanning mirrors 82–84. This proportional relationship between the angular displacement of the scanning mirrors 82, 84 and the linear displacement of the focusing point on the plane of the conveyor provides for relatively easy and efficient control in directing the laser pulses to selected locations within the target area. Lenses designed with this desired distortion characteristic are generally known as F-Theta lenses.

A telecentric F-Theta lens may also be utilized as the focusing element 86. In addition to providing the above-described advantages, this type of F-Theta focusing lens provides a focused laser beam whose axis is perpendicular to the scanning plane of the target area throughout the target area. This arrangement is particularly advantageous since in the present scrap metal sorting system, the angular relationship between the laser pulse stream and the particles' surface would be consistent, and would not depend upon the particles' location. Thus, by utilizing a telecentric F-Theta lens, more uniform plasma characteristics, as well as simpler design geometries for the collection optics, may be achieved.

Thus, the use of a telecentric F-Theta lens reduces the non-uniformity which may arise from different particles being ablated by laser pulses striking the particles from different angles. Similarly, by providing each of the plurality of pulses to each particle without repositioning the beam, more uniformity in the results is achieved for each particle.

A plurality of target scanner assemblies 22 (shown in FIG. 2) are preferably provided. The number of scanner assemblies is dependent upon the number and location of scrap particles passing through the target area(s) for ablation, which in turn is dependent upon the density of the particles on the conveyor, the size of the conveyor, and the speed of the conveyor. In the embodiment illustrated in FIG. 2, three target scanner assemblies 22 are utilized and are positioned generally across the width of a 25–30 inch wide conveyor 12. In this embodiment, each of the scanners covers a generally square target area of approximately 10 inches on each side. Again, it will be appreciated that the scanner assemblies may be arranged so that the target areas covered by each of the scanner assemblies overlaps thereby providing additional opportunities for firing laser pulses at each scrap particle which moves through the overlapping areas. Similarly, the scanner assemblies can be arranged so that their target areas cover the same areas across the width of the conveyor belt, with the target area of one scanner assembly being relatively downstream of the target area of another scanner assembly. Again, this arrangement will provide with additional firing opportunities for each scrap particle, thereby increasing the potential sorting rate for the system.

Thus, it should be appreciated that a system of the present invention employing a pool of laser systems along with a plurality of target scanner assemblies having overlapping target areas, insures that system performance will not be constrained by any single device, such as by the pulse frequency of the laser, or by the speed or target area size of a particular scanner assembly.

It should be noted that, although the preferred embodiments employ galvanometric scanners with mirrors as beam deflectors, it is contemplated that other beam deflectors, such as acousto-optical deflectors, may be suitable for use in place of, or in conjunction with, mirrors in the various scanner assemblies.

Figure 8:
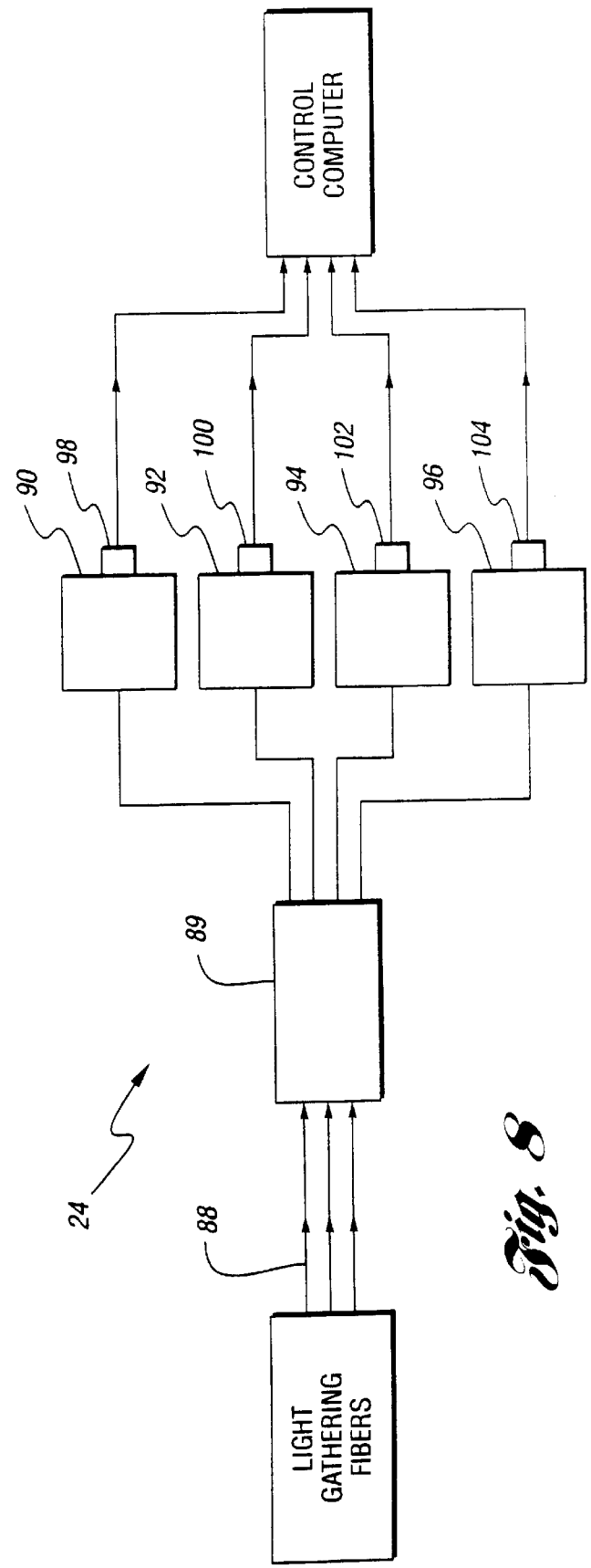
FIG. 8 is a diagram of the light distribution and spectral analysis unit.

Referring now to FIGS. 6 and 8, the light collector 26 preferably employed by the system of the present invention includes a plurality of ultraviolet grade fused-silica optical fibers 88 which are positioned, preferably in the scanner housings (as shown in FIG. 6), to collect light from the plasma created as a result of ablation of the scrap particles. The optical fibers 88 are positioned in such a way that effects due to particle orientation and location are minimized. The fibers 88 are distributed to collect light over each of the target areas. In the illustrated embodiment, the light-gathering fibers 88 supply collected light from the plasma to a light distribution and spectral analysis system 28, which may include an integrating chamber 89. The integrating chamber 89 provides an even uniform distribution of the collected light to each of one or more spectral filters 90–96, preferably comprising a plurality of monochromater systems. In the embodiment of FIG. 8, each of the monochromaters 90–96 transmits a narrow band (approximately 0.05 to 0.1 nanometers) centered around a selected frequency to a detector 98–104 which provides an analog signal to the control 30 corresponding to the intensity of the emission of the associated monochromater. In the embodiment shown in FIG. 8, monochromater Model No. 270M, available from Spex Industries, of Edison, N. J., U.S.A. are utilized as spectral filters 90–96. Photomultiplier tubes (PMTs) capable of detecting pulsed radiation, available from Hamamatsu, Inc., are used as detectors 98–104.

It will be appreciated that, though the illustrated embodiment of the light distribution and spectral analysis system 28 utilizes an integrating chamber 89, the integrating chamber is optional. The integrating chamber is used in the illustrated embodiment to provide a uniform distribution of light to the various monochromater systems. However, the design and complexity of the light distribution system may vary, depending upon the number of monochromater systems used and the number and locations from which the light is collected. For example, a system might employ a simple optical coupling between a randomized optical fiber bundle collecting light and a randomized optical fiber bundle distributing light to more complex integrating sphere systems such as ones that are available from Labsphere, Inc. Alternatively, the integrating chamber could be eliminated in a system that uses a single polychromater in place of the plurality of monochromaters. Other light gathering, light detection, light distribution, light dispersion, light filtering, and spectral data components may be provided in various arrangements without departing from the spirit of the invention. For example, liquid light guides may be utilized in place of the optical fibers for collecting and/or distributing the light. Similarly, spectrographs, optical band-pass filters, or polychromaters may be utilized as spectral filters 90–96 in place of monochromaters. Also, solid-state detectors such as photodiodes, may be utilized in place of the PMTs, and/or intensified diode arrays and CCD detectors may be used in conjunction with spectrograph systems for array detection, all without departing from the spirit of the present invention. It will also be appreciated that multiple sets of the light distributing systems shown in FIG. 8 may be utilized as required, based upon the size and speed of the conveyor, as well as the density of scrap particles on the conveyor.

Referring again to FIGS. 1 and 2, once the light distributor and spectral analyzer 28 have provided the control 30 with the spectral data for a selected scrap particle and the data has been analyzed as described below, a discriminator signal is provided to the separator 32 at a time and location suitable to direct that scrap particle into the appropriate direction to sort the particle. In the illustrated embodiment, the separator 32 comprises one or more arrays of conventional air nozzles 106–110, which are mounted across the width of the discharge end of the conveyor, and are utilized along with a conventional splitter box 112 to separate the particles as they exit the conveyor. In this embodiment, selected air nozzles in the arrays 106–110 are activated at the appropriate location across the width of the conveyor to provide a blast of air (or other suitable gas) sufficiently strong to urge a targeted scrap particle into one of the channels in the splitter box 112 to direct the particle to the appropriate bin 114–118, or, where appropriate, no blast of air is provided at the location of a selected falling scrap particle to allow the particle to free fall into bin 120.

In the embodiment of FIG. 1, three air nozzle assemblies are utilized to effectively sort the scrap particles into four categories. The discharge end of the air nozzles are preferably connected to an ejector plate or other rigid spacing mechanism to insure that the nozzles are equally spaced apart from each other across the width of the conveyor belt. The distance between the air nozzles is, of course, dependent upon the size of the particles being sorted. However, the spacing should be suitable so that at least one of the air nozzles may be activated at a selected time to provide an air jet adequate to propel a selected scrap particle into the desired bin. It will be appreciated that there are various other conventional separator mechanisms, including single air nozzle assemblies, pusher arms, etc., which may also be utilized as the separator 32 without departing from the spirit of the invention. One such alternate air nozzle assembly is disclosed in co-pending U.S. patent application Ser. No. 08/176,018, for a "Scrap Sorting System," filed on Dec. 30, 1993, which disclosure is hereby incorporated herein for this purpose.

An air moving device (not shown) for drawing or blowing air, may be placed underneath the target scanner assemblies 22 just above the conveyor belt 12 to remove ablated particles, metallic dust, dirt, etc., from the target area and to reduce any long term deposits from occurring on any of the optical components of the beam deflectors in the scanner assemblies 22 or the light collectors 26.

Referring again to FIG. 1, the lighting fixture 38 preferably includes a generally semi-cylindrical opaque shroud 122 fabricated from suitable structural material, such as aluminum or sheet metal. In one embodiment, eight fluorescent lamps 124 are mounted within the shroud 122. One or more fans (not shown) with suitable filters may be mounted within the shroud 122 to remove heat, dust and debris from the viewing area. A series of photodetectors (not shown) are also preferably mounted within the shroud, and are operably connected to commercially available lamp controllers to provide a constant feedback signal indicating the level of illumination within the shroud. The outside of the shroud 122 is opaque. The inside is preferably covered with light diffuser material to provide for diffuse, even lighting of the viewing area 16.

It will be appreciated that various lighting arrangements may be employed, depending upon the size of the viewing area 16 and the imaging information desired to be collected. In the embodiment of FIG. 1, the semicircular shroud 122, includes a plurality of generally evenly spaced elongate fluorescent lamps each of which extends across the width of the conveyor belt, illuminates the narrow viewing area from which images are collected by the linescan camera 36 with sufficiently uniform, intense, multidirectional and diffused light to provide consistent and reliable image data from which the shape, size and location of particles can be determined. It must be understood that the overall intent is to provide an illumination scheme which will aid the linescan camera to register an accurate two-dimensional outline of particles that have complex and irregular shapes, with widely varying reflectivities, such as are present in the scrap metal particles sorted by the present system. Alternative arrangements, such as are disclosed in U.S. application Ser. No. 08/176,018, for a "Scrap Sorting System," filed Dec. 30, 1993, and incorporated herein to the extent of such disclosure, may be utilized to obtain image information over a wider viewing area, including color information relating to the particles, if desired.

Figure 9:
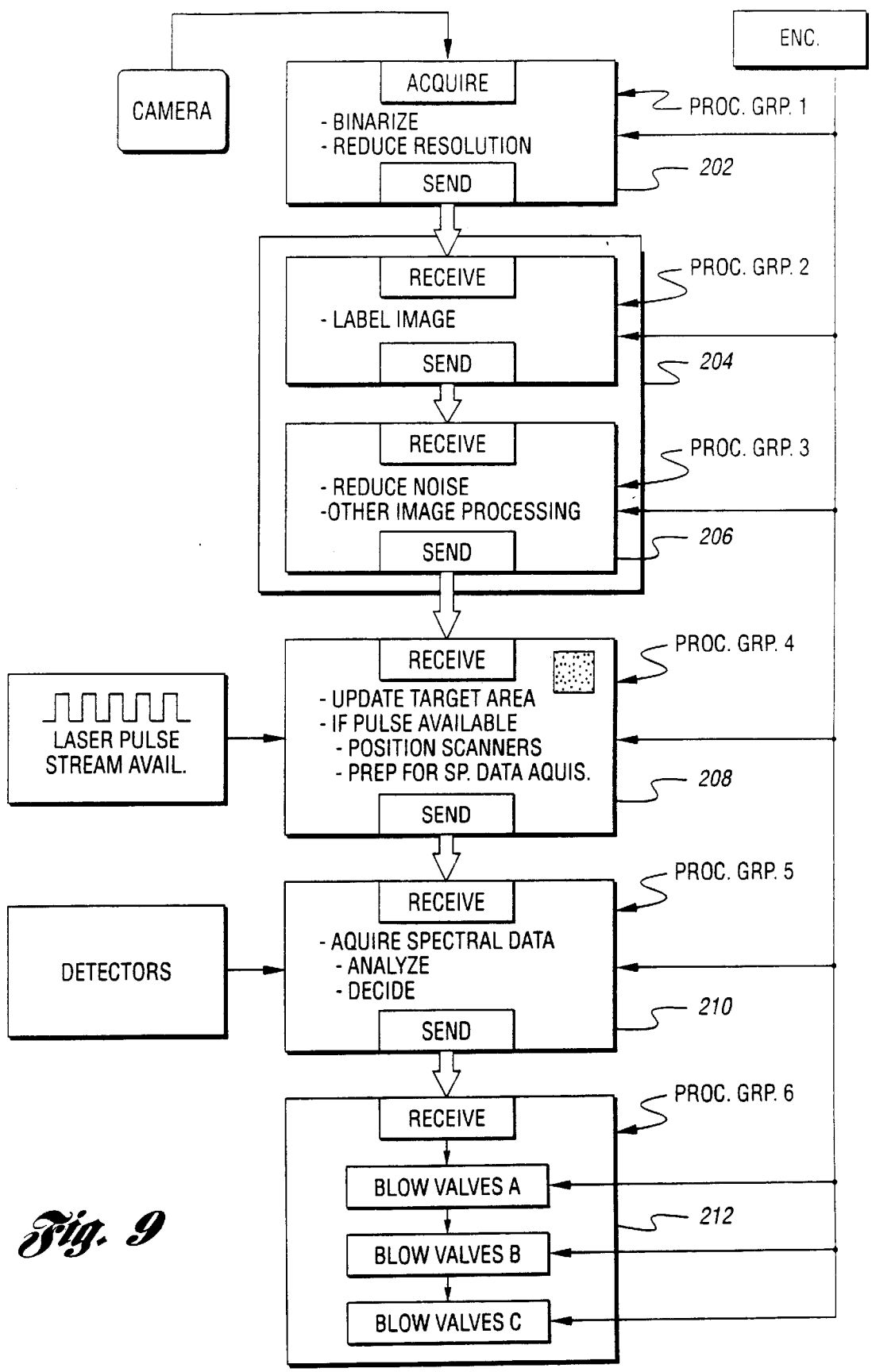
FIG. 9 is a diagram illustrating the functions performed by the system control.

FIG. 9 is a functional block diagram illustrating the basic functions performed by the control 32. As previously described, various hardware and software configurations may be employed to perform the control functions described herein. In one embodiment, a networked computer system employing a plurality of processors is utilized to achieve a high-speed, multi-tasking environment in which processing takes place continuously and simultaneously on a number of different processors. Each processor in turn is capable of providing a multi-tasking environment where a number of functionally different programs could be simultaneously active, sharing the processor on a priority and need basis. In this embodiment, the basic functions have been divided into process groups (illustrated as PROC.GRP.1–PROC.GRP.6) which indicate functional divisions of the processing tasks required by the system. Each of these process groups could be implemented on hardware utilizing at least one dedicated programmable processor for that group. Alternatively, particularly for simpler sorting systems, all of the process groups could be implemented on hardware utilizing a single processor on a shared basis. It will, of course, be appreciated that the choice of implementation of hardware to support the functions identified in the process groups will depend upon the size and speed of the system, as well as upon the categories being sorted.

Beginning at 202, the system continuously acquires digital image data from the linescan camera and performs conventional techniques to create a binary representation of preferably 1024×1 pixels, based upon the linescan data. Again, conventional resolution reduction techniques are utilized to reduce the image data for more efficient extraction of the desired image information during the image processing operations. The reduced binary image data is then sent to the next hardware platform which is suitably programmed to perform the image processing functions identified at 204. In one embodiment, a conventional labelling process is performed on the image to identify and label each of the scrap particles in the image. This image data is then sent to the next hardware platform, indicated at 206, to perform a conventional noise reduction image processing operation on the image.

It should be appreciated that, contrary to the typical order of processing an image, it is desirable under the present circumstances to perform the noise reduction operation on the image after the labeling operation has been performed. In this way, scrap particles having shapes which include, for example, two relatively sizeable areas connected by a very narrow intermediate portion, will be labeled as one piece, even if subsequent noise reduction techniques eliminate the data representing the very narrow intermediate portion. Thus, basic particle identification is maintained even if subsequent noise reduction techniques show a particular particle as multiple separate pieces. This order of image processing is particularly useful where, as in the present application, particles of unknown size and widely irregular shape, are being identified and labeled through image processing.

Other image processing functions, such as conventional shape and feature extraction, may be performed on the images. Shape and feature information may, for example, be utilized to identify preferred locations for ablating the particle. This image information may also be utilized as additional input, at 210, for analysis and categorization of the particles.

As indicated at 208, the system receives the processed image data, preferably on a separate hardware platform, and utilizes the data to continuously update an image window of the target areas for each of the scanner assemblies 22 employed by the system. The system monitors input from the laser system(s) to determine when the next laser pulse stream will be available. When the next laser pulse stream is available, the system scans the updated target area window(s) to determine the existence and location of any scrap particles within the target areas for any of the scanner assemblies 22. If a particle which has not been ablated appears in any of the target area windows, the system then generates the required control signals to operate the scanners in the scanner assemblies as appropriate to direct the pulse stream to the desired location, based upon the position data relating to the identified particle. The system also transmits the appropriate signals to indicate to the light distribution and spectral analysis system 28 associated with the selected scanner assembly 22 to prepare for spectral data acquisition from that scanner assembly's target area.

As indicated at 210, the system, preferably on a separately programmed hardware platform, performs the spectral data acquisition. In the embodiment shown in FIGS. 1, 2 and 8, the spectral data is derived from the outputs of the detectors 98–104 associated with the monochromaters 90–96 in the light distribution and spectral analysis system 28. This information may consist of intensities relating to one or more selected narrow bands of spectral emission recognized by the monochromaters. In one embodiment, the spectral data is collected for each one of four laser pulses. The specific spectral lines that are observed, the delay time (gate delay) from the firing of the pulse when observations begin, and the time duration (gate width) during which data is collected, all depend on the elements that are required to be identified in the scrap particles. The selection of these parameters has been researched, and is the topic of several relevant publications, including "The Analysis of Metals at a Distance Using Laser-Induced Breakdown Spectroscopy" David A. Cremers, Applied Spectroscopy, Vol. 41, No. 4, May/June, 1987; and "Quantitative Analysis of Aluminum Alloys by Laser-Induced Breakdown Spectroscopy and Plasma Characterization," Mohamad Sabsabi and Paolo Cielo, Applied Spectroscopy, Vol. 49, No. 4, 1995.

The analog output of the detectors is sampled at a high enough sampling interval to provide a generally accurate digital representation of the analog waveform. The exact sampling duration will depend upon the elements being detected. In one embodiment, sampling intervals of about 10 to 20 nanoseconds are employed.

It is desirable to separate the laser pulses with a sufficient waiting period so as to allow the spectral excitation from the plasma emitted as a result of the previous pulse to abate sufficiently so that the spectral data acquired following the next pulses is not affected by the previous pulse. In one embodiment, as disclosed in FIG. 4, it has been found that separating the laser pulses by about 50 microseconds provides adequate time (about 2 to 3 microseconds) to collect spectral data from the most recent pulse, and adequate additional waiting time thereafter to insure that the spectral data collected following the next pulse is reliable. The gate delay following a laser pulse should be sufficiently long (at least about 0.5–3 microseconds) so as to eliminate the less reliable data typically acquired at the moment of ablation. It will similarly be appreciated that the waiting period after collection of spectral data from a particular pulse and before the next pulse should be long enough to insure that two distinct readings are recorded for each of the separate pulses, yet not so long that the total time for firing and data acquisition for the desired number of pulses for a particular particle is not so long that repositioning of the scanners is required.

Once the spectral data is acquired, the system then analyzes the data for the multiple pulses for each particle as previously described herein. Again, the type and scope of data analysis can vary, utilizing in each case known regimes, depending upon the different types of particles that are being sorted. For example, two categories of scrap particles may be distinguished and sorted by isolating one or two spectral bands and utilizing simple ratioing techniques. In contrast, sorting several categories of particles that have similar constituents, such as several different aluminum alloys, may require the utilization of a more complex classification regime, such as a neural network, which receives inputs relating to a plurality of selected spectral lines, as well as other (shape, color, etc.) inputs to categorize the particles.

As a result of the analysis, the particle is then categorized, and a discriminator signal is sent to the separator control.

The discriminator signal includes encoded data which identifies the location of the particle and the category of the particle. This data is received, at 212, by the separator control logic which, at the suitable time, based upon the continuous encoder input, activates one or more appropriate air nozzle(s) (or does not activate any of the nozzles), as required, to move the selected particle as required into the appropriate bin with other particles of that category.

It should be noted that, although the control functions are shown in a sequence of blocks 202–212, each of the functions may be operating simultaneously in real-time. For example, digital image data is continuously acquired from the image detector on a line-by-line basis so long as the conveyor belt is moving. The image processing function, at 202, accumulates the linescan data into buffers of a suitable size to efficiently binarize and reduce the image. Once processed, the image data is sent to processing group II, again preferably on a line-by-line basis. Again, the image processing operations, including labeling and noise reduction, performed at 204, may be performed on a buffer of image data of a size suitable to efficiently process the image. The data is then sent to process group IV, again preferably on a line-by-line basis where it is again continually buffered into images each the size of each of the target areas. It will thus be appreciated that image data is thus sequentially flowing, on a line-by-line basis, between processing groups I through IV, each of the processing functions may be continually changing and processing buffered sets of the data.

As previously described, the control 30 includes analyzing/decision-making logic to develop an output identifying the particle based upon the spectral data input from the detectors 98–104 in each light collector 26. Additionally, one of the monochromater/detectors in each light collector might be utilized to transmit a value corresponding to the amount of scattered radiation at the operating wavelength of the lasers in addition to the selected emission lines monitored by other monochromaters/detectors. Also, other information, including laser energy produced, and particle location, as well as the geometric features and color information developed for a selected particle from image data acquired by the camera 36, may be utilized as input to the analyzing/decision-making logic of the control 30.

As previously described, the analyzing/decision-making logic may utilize simple known rationing techniques to classify each particle into a metal/alloy category. In this approach, the intensities of one or more analyte spectral lines (observed for a specified period of time after the laser radiation strikes the surface of the particle) are compared to the intensity of a reference line. These ratios would then be compared to different ranges of values corresponding to the different alloys to categorize the particle.

In order to improve the accuracy of classification, the logic may employ a more complex classification scheme, such as a neural network. Known neural network programs may be "trained" to "learn" relationships between groups of input and output data by running the neural network through a "supervised learning" process. The relationships thus learned could then be used to predict outputs (i.e., categorize each of the scrap particles) based upon a given set of inputs relating to, for example, emission intensities and scatter produced from representative samples of scrap having known chemistry.

Figure 10:
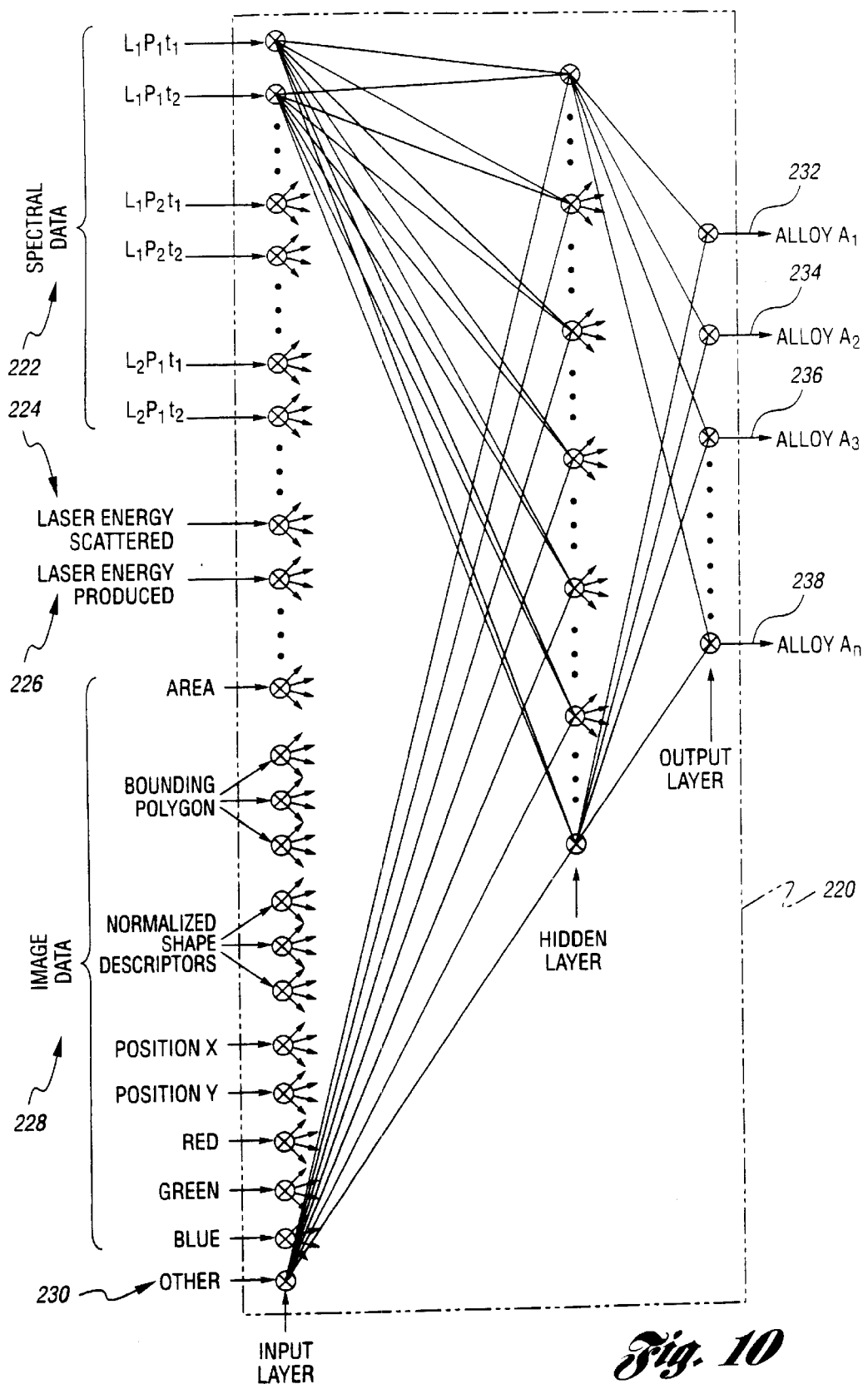
FIG. 10 is a diagram of a basic neural network which may be employed by the system to perform the analysis and categorization of the particles.

Referring to FIG. 10, the analyzing/decision-making logic may employ a neural network classifier algorithm. Commercially available neural network configuration tools may be employed to establish a known generalized functional relationship between sets of input and output data. Known algorithmic techniques such as back propagation and competitive learning, may be applied to estimate the various parameters or weights for a given class of input and output data. As illustrated in FIG. 10, a neural network 220 may be configured to include the spectral data acquired by the control from the light distribution and spectral analysis system 28 as data inputs. For example, the multiple inputs 222 corresponding to the spectral data for a selected particle might include a series of data inputs corresponding to intensity readings from a detector for a selected spectral band (L) over a selected period of time (t) following the first pulse (P) $(L_1P_1t_1, L_1P_1t_2 \ldots L_1P_1t_n)$, data corresponding to detector readings for the same selected band following the second pulse $(L_1P_2t_1, L_1P_2t_2 \ldots L_1P_2t_n)$, and similar data inputs for that selected spectral band for each additional pulse directed to the particle $(L_1P_nt_1, L_1P_nt_2 \ldots L_1P_2t_n)$, as well as additional of these sets for each of the selected bands $(L_2P_1t_1 \ldots L_2P_nt_n, L_nP_1t_1 \ldots L_nP_nt_n)$, and so on.

The neural network 220 may also be provided with a variety of other desired inputs, including spectral data inputs 222, data relating to laser energy scattered, 224, data related to laser energy produced, 226, and various image data, shown at 228 for each particle. The image data may include the area of the particle, and the dimensions of a bounding polygon, normalized shape descriptors, the position of the particle, as well as color information, if desired. Similarly, other inputs 230 deemed influential to the decision-making process might be included. As previously described, using known neural network programming techniques, the network can be trained by providing sets of the inputs along with the desired one of possible outputs 232–238. Once the specific functional relationships between the inputs and outputs are obtained, the network may be used with new sets of input to predict output values. It will be appreciated that once developed, the neural network may incorporate information from a multitude of inputs into the decision-making process to categorize particles in an efficient manner.

It will thus be appreciated that the system of the present invention provides a means for sorting irregularly shaped scrap metal particles on a rapidly moving conveyor based upon the optical analysis of laser-induced plasmas. The pulses are focused along a plane, thereby insuring that particles traveling on a generally planar conveyor, are ablated with laser pulses of uniform power densities. And, by utilizing scanner assemblies including F-Theta lenses, simple efficient control of the scanners is attained, since the uniform rotation of the deflector is transformed into a uniform scan across the target area. Moreover, the utilization of solid-state, fixed-frequency lasers, preferably operating in double-pulse mode, provides for the rapid availability of sets of pulses which may be directed to ablate a selected particle as it moves through a target location without repositioning the scanners.

While the best mode for carrying out the invention has been described in detail, those familiar with the art to which this invention relates will recognize various alternative designs and embodiments for practicing the invention as defined by the following claims.

What is claimed is:

1. A system for sorting randomly positioned scrap particles on a moving conveyor, the system including:
   an image detector for locating scrap particles as they pass through a predefined viewing area on the conveyor;
   a position detector for detecting movement of the conveyor;

a laser system including at least one laser to periodically provide a laser beam including a plurality of laser pulses within a selected time interval;

at least one target scanner assembly mounted to direct focused laser pulses to a selected location within a two-dimensional target area on the conveyor downstream from the viewing area, said at least one target scanner assembly including a beam deflector mounted in the path of the laser pulses, and a focusing element mounted in the path of the laser pulses downstream from the beam deflector to focus the laser pulses and provide a generally uniform power density from the pulses along a plane;

a light collector for receiving light in the target area from plasma generated by said laser pulses;

a light distribution and spectral analyzer system for isolating and measuring at least one selected band from the light collected by the light collector, the light distribution and spectral analyzer system including at least one spectral filter operably connected to the light collector to transmit a band of selected frequency to a detector which provides a signal corresponding to the intensity of the emission of the spectral filter;

a separator; and a control including logic for processing the image data acquired from the image detector to identify scrap particles as the particles pass through the viewing area on the moving conveyor, continuously monitoring the positions of each of the identified particles on the moving conveyor based on information received from the position detector, continuously monitoring the laser system to determine when the next plurality of pulses will be produced, and when pulses are available, locating a scrap particle at least one target area, generating the control signals necessary to operate the at least one target scanner assembly to direct the next plurality of pulses to irradiate the located scrap particle, wherein the selected time interval of the pulses allows each pulse to strike the particle without re-positioning the beam deflector in the scanner assembly, analyzing the spectral data thereafter received from the target location, generating a discriminator signal based on the results of the spectral data analysis, and selectively activating the separator as a function of the discriminator signal to sort the scrap particles.

2. The system of claim 1 wherein the laser system includes two solid-state fixed frequency lasers synchronized to periodically provide the plurality of laser pulses within the selected time interval.

3. The system of claim 2 wherein each of the lasers in the laser system are operating in double-pulse mode.

4. The system of claim 2 wherein the lasers are capable of generating at least four pulses within the selected time interval.

5. The system of claim 1 wherein the selected time interval is less than about 250 microseconds.

6. The system of claim 1 wherein the beam deflector comprises at least two galvanometric scanners, each scanner including a positionable mirror, each of the mirrors mounted in the path of the laser pulses.

7. The system of claim 1 wherein the focusing element comprises an F-Theta lens.

8. The system of claim 1 wherein the focusing element comprises an F-Theta telecentric lens.

9. The system of claim 1 wherein the spectral filter includes at least one monochromater.

10. The system of claim 1 wherein the spectral filter includes a polychromater.

11. The system of claim 1 wherein the detector is a photomultiplier tube.

12. The system of claim 1 wherein the signal provided by the detector is acquired by the control using a high speed analog-to-digital converter.

13. The system of claim 1 wherein a plurality of target scanner assemblies are utilized, and wherein the combined target areas of the target scanner assemblies cover substantially the entire width of the conveyor.

14. The system of claim 1 wherein the light collector includes a plurality of optical fibers.

15. The system of claim 1 wherein the image detector includes a linescan camera and a light system which provides uniform illumination of the viewing area.

16. The system of claim 15 wherein the position detector is an encoder, and wherein the linescan camera acquires a linescan of the viewing area at each pulse of the encoder.

17. The system of claim 1 wherein the separator comprises a plurality of air nozzles generally equally spaced across the width of the conveyor, which air nozzles may be selectively and independently controlled to provide an air blast at a selected time to urge a selected scrap particle into a desired path.

18. The system of claim 1 wherein the separator comprises a plurality of air nozzle assemblies, each air nozzle assembly comprising a plurality of air nozzles generally equally spaced across the width of the conveyor, which air nozzles may be selectively and independently controlled to provide an air blast at a selected time to urge a selected scrap particle into a selected path, and wherein the selected path of each of the air nozzle assemblies is different, whereby the scrap particles may be sorted into a plurality of categories.

19. The system of claim 18 wherein the separator comprises three air nozzle assemblies mounted for separating the particles into four separate categories.

20. The system of claim 1 wherein the logic employs a ratioing regime for analyzing the spectral data received from the target location.

21. The system of claim 1 wherein the logic employs a neural network for analyzing the spectral data received from the target location.

22. The system of claim 21 wherein the neural network receives other data inputs in addition to the spectral data inputs.

23. The system of claim 22 wherein the other data inputs include data corresponding to laser energy scattered and laser energy produced in connection with each particle.

24. The system of claim 22 wherein the other data inputs include image data relating to each of the particles.

25. The system of claim 1 wherein the control logic includes logic for analyzing image information relating to a particle, and wherein the logic for generating a discriminator signal is based upon the image data analysis as well as the spectral data analysis for a particle.

26. The system of claim 1 wherein the control includes hardware comprising a plurality of processors that are networked to provide the capability for simultaneous processing of multiple control functions.

27. A system for sorting randomly positioned scrap metal particles on a moving conveyor including:

an image detector for locating scrap particles as they pass through a predefined viewing area on the conveyor;

a position detector for detecting movement of the conveyor;

a laser pool comprising a plurality of laser systems, each laser system including at least one laser to periodically provide a laser beam including a plurality of laser pulses within a selected time interval;

at least one target scanner assembly, said at least one target scanner assembly mounted to direct the laser pulses to a selected location within a two-dimensional target area on the conveyor downstream from the viewing area, said at least one target scanner assembly including a beam deflector mounted in the path of the laser pulses, and a focusing element mounted in the path of the laser pulses downstream from the beam deflector to focus the laser pulses and provide a generally uniform power density from the pulses along a plane;

a light collector associated with said at least one target scanner assembly, the light collector mounted to receive light from plasma generated by said laser pulses in the target area of the associated scanner assembly;

a light distribution and spectral analyzer system for isolating and measuring at least one selected band from the light collected by the light collector, the light distribution and spectral analyzer system including at least one spectral filter operably connected to the light collector to transmit a band of selected frequency to a detector which provides a signal corresponding to the intensity of the emission of the spectral filter;

a separator; and a control including logic for processing the image data acquired from the image detector to identify scrap particles as the particles pass through the viewing area on the moving conveyor, continuously monitoring the positions of each of the identified particles on the moving conveyor based on information received from the position detector, continuously monitoring each laser system in the pool to determine when the next plurality of pulses will be produced, and when pulses are available, locating a scrap particle in at least one target area, generating the control signals necessary to operate the at least one target scanner assembly to direct the next plurality of pulses to irradiate the located scrap particle, wherein the selected time interval allows each pulse to strike the particle without repositioning the beam deflector in the scanner assembly, analyzing the spectral data thereafter received from the target location, generating a discriminator signal based on the results of the spectral data analysis, and selectively activating the separator as a function of the discriminator signal to sort the scrap particles.

28. The system of claim 27 wherein each laser system includes two solid-state fixed frequency lasers synchronized to periodically provide the plurality of laser pulses within the selected time interval.

29. The system of claim 28 wherein each of the lasers in each laser system are operating in double-pulse mode.

30. The system of claim 28 wherein the lasers are capable of generating at least four pulses within the selected time interval.

31. The system of claim 27 wherein the selected time interval is less than about 250 microseconds.

32. The system of claim 27 wherein the beam deflector comprises at least two galvanometric scanners, each scanner including a positionable mirror, each of the mirrors mounted in the path of the laser pulses.

33. The system of claim 27 wherein the focusing element comprises an F-Theta lens.

34. The system of claim 27 wherein the focusing element comprises an F-Theta telecentric lens.

35. The system of claim 27 wherein the spectral filter includes at least one monochromater.

36. The system of claim 27 wherein the spectral filter includes a polychromater.

37. The system of claim 27 wherein the detector is a photomultiplier tube.

38. The system of claim 27 wherein the signal provided by the detector is acquired by the control using a high speed analog-to-digital converter.

39. The system of claim 27 wherein a plurality of target scanner assemblies are utilized, and wherein the combined target areas of the target scanner assemblies cover substantially the entire width of the conveyor.

40. The system of claim 27 wherein the light collector includes a plurality of optical fibers.

41. The system of claim 27 wherein the image detector includes a linescan camera and a light system which provides uniform illumination of the viewing area.

42. The system of claim 41 wherein the position detector is an encoder, and wherein the linescan camera acquires a linescan of the viewing area at each pulse of the encoder.

43. The system of claim 27 wherein the separator comprises a plurality of air nozzles extending across the width of the conveyor, which air nozzles may be selectively and independently controlled to provide an air blast at a selected time to urge a selected scrap particle into a desired path.

44. The system of claim 27 wherein the separator comprises a plurality of air nozzle assemblies, each air nozzle assembly comprising a plurality of air nozzles generally equally spaced across the width of the conveyor, which air nozzles may be selectively and independently controlled to provide an air blast at a selected time to urge a selected scrap particle into a selected path, and wherein the selected path of each of the air nozzle assemblies is different, whereby the scrap particles may be sorted into a plurality of categories.

45. The system of claim 44 wherein the separator comprises three air nozzle assemblies mounted for separating the particles into four separate categories.

46. The system of claim 27 wherein the logic employs a ratioing regime for analyzing the spectral data received from the target location.

47. The system of claim 27 wherein the logic employs a neural network for analyzing the spectral data received from the target location.

48. The system of claim 47 wherein the neural network receives other data inputs in addition to the spectral data inputs.

49. The system of claim 48 wherein the other data inputs include data corresponding to laser energy scattered and laser energy produced in connection with each particle.

50. The system of claim 48 wherein the other data inputs include image data relating to each of the particles.

51. The system of claim 27 wherein the control logic includes logic for analyzing image information relating to a particle, and wherein the logic for generating a discriminator signal is based upon the image data analysis as well as the spectral data analysis for a particle.

52. The system of claim 27 wherein the control includes hardware comprising a plurality of processors that are networked to provide the capability for simultaneous processing of multiple control functions.

53. A system for sorting randomly positioned scrap metal particles on a moving conveyor, the system including:

an image detector for locating scrap particles as they pass through a predefined viewing area on the conveyor, the image detector including a linescan camera and a light system which provides uniform illumination of the viewing area;

a position detector for detecting movement of the conveyor;

a laser system including at least one solid-state fixed frequency laser configured to periodically provide a laser beam including a plurality of laser pulses within a selected time interval;

a plurality of target scanner assemblies, each target scanner assembly mounted to direct focused laser pulses to a selected location within a two-dimensional target area on the conveyor downstream from the viewing area, each target scanner assembly including a beam deflector comprising at least two galvanometric scanners, each scanner including a positionable mirror, each of the mirrors mounted in the path of the laser pulses, and a focusing element comprising an F-Theta lens mounted in the path of the laser pulses downstream from the beam deflector to focus the laser pulses and provide a generally uniform power density from the pulses along a plane, wherein the combined target areas of the target scanner assemblies cover substantially the entire width of the conveyor;

a light collector including a plurality of optical fibers for receiving light in the target areas from plasma generated by said laser pulses;

a light distribution and spectral analyzer system for isolating and measuring at least one selected band from the light collected by the light collector, the light distribution and spectral analyzer system including a spectral filter having at least one monochromater operably connected to the light collector to transmit band of selected frequency to a detector which provides a signal corresponding to the intensity of the emission of the spectral filter;

a separator; and a control including logic for processing the image data acquired from the image detector to identify scrap particles as the particles pass through the viewing area on the moving conveyor, continuously monitoring the positions of each of the identified particles on the moving conveyor based on information received from the position detector, continuously monitoring the laser system to determine when the next plurality of pulses will be produced, and when pulses are available, locating a scrap particle in one of the target areas, generating the control signals necessary to operate the appropriate target scanner assembly to direct the next plurality of pulses to irradiate the located scrap particle, wherein the selected time interval of the pulses allows each pulse to strike the particle without re-positioning the mirrors in the scanner assembly, analyzing the spectral data thereafter received from the target location, generating a discriminator signal based on the results of the spectral data analysis, and selectively activating the separator as a function of the discriminator signal to sort the scrap particles.

54. A method for sorting randomly positioned scrap particles on a moving conveyor in a system including, the method including;

locating scrap particles as they pass through a predefined viewing area on the conveyor by periodically acquiring a digital image of the viewing area;

detecting movement of the conveyor;

providing a laser system including at least one laser to periodically provide a laser beam including a plurality of laser pulses within a selected time interval;

directing focused laser pulses to a selected location within a two-dimensional target area on the conveyor downstream from the viewing area, using at least one target scanner assembly including a beam deflector mounted in the path of the laser pulses, and a focusing element mounted in the path of the laser pulses downstream from the beam deflector to focus the laser pulses and provide a generally uniform power density from the pulses along a plane;

collecting light in the target area from the generated plasma;

isolating and measuring at least one selected band from the collected light using a light distribution and spectral analyzer system including at least one spectral filter operably connected to the light collector to transmit a band of selected frequency to a detector which provides a signal corresponding to the intensity of the emission of the spectral filter;

providing an actuable separator for selectively directing the particles along different sort paths as they reach the end of the conveyor; and processing each acquired image to identify scrap particles as the particles pass through the viewing area on the moving conveyor, continuously monitoring the positions of each of the identified particles on the moving conveyor based on the detected movement of the conveyor, continuously monitoring the laser system to determine when the next plurality of pulses will be produced, and when pulses are available, operating at least one target scanner assembly to direct the next available plurality of pulses to irradiate an identified scrap particle, wherein the selected time interval of the pulses allows each pulse to strike the particle without re-positioning the beam deflector in the scanner assembly, analyzing the spectral data thereafter received from the target location, and selectively activating the separator based on the results of the spectral data analysis to sort the scrap particles.

55. The method of claim 54 wherein the laser beam is provided to include at least four pulses within a time interval of about 250 microseconds.

56. The method of claim 54 wherein analyzing the spectral data includes employing a ratioing regime.

57. The method of claim 54 wherein analyzing the spectral data includes employing a neural network.

58. The method of claim 54 further including analyzing image data relating to a selected particle, and wherein the separator is selectively activated based upon the results of the image data analysis as well as the spectral data analysis.

59. A system for sorting randomly positioned scrap particles on a moving conveyor, the system including:

an image detector for locating scrap particles as they pass through a predefined viewing area on the conveyor;

a position detector for detecting movement of the conveyor;

a laser system including a laser to periodically provide a laser beam including a plurality of laser pulses within a selected time interval;

a target scanner assembly mounted to direct focused laser pulses to a selected location within a two-dimensional target area on the conveyor downstream from the viewing area;

a light collector for receiving light in the target area from the plasma generated by said laser pulses;

a light distribution and spectral analyzer system for isolating and measuring at least one selected band from the light collected by the light collector;

a separator; and a control including logic for processing the image data acquired from the image detector to identify scrap particles as the particles pass through the viewing area on the moving conveyor, monitoring the positions of each of the identified particles on the moving conveyor based on information received from the position detector, monitoring the laser system to determine when the next plurality of pulses will be produced, and when pulses are available, locating a scrap particle in the target area, generating the control signals necessary to operate the target scanner assembly to direct the next plurality of pulses to irradiate the located scrap particle, wherein the selected time interval of the pulses allows each pulse to strike the particle without re-positioning the beam deflector in the scanner assembly, analyzing the spectral data thereafter received from the target location, generating a discriminator signal based on the results of the spectral data analysis, and selectively activating the separator as a function of the discriminator signal to sort the scrap particles.

60. A method for sorting randomly positioned scrap particles on a moving conveyor, the method including;

locating scrap particles as they pass through a predefined viewing area on the conveyor by periodically acquiring a digital image of the viewing area;

detecting movement of the conveyor;

providing a laser system including at least one laser to periodically provide a laser beam including a plurality of laser pulses within a selected time interval;

directing focused laser pulses to a selected location within a two-dimensional target area on the conveyor downstream from the viewing area, and focusing the laser pulses to provide a generally uniform power density from the pulses along a plane;

collecting light from the selected locations in the target area from the plasma generated by the laser pulses;

isolating and measuring at least one selected band from the collected light, and providing a signal corresponding to the intensity of the emission of the selected band;

providing an actuable separator for selectively directing the particles along different sort paths as they reach the end of the conveyor; and processing each acquired image to identify scrap particles as the particles pass through the viewing area on the moving conveyor, continuously monitoring the positions of each of the identified particles on the moving conveyor based on the detected movement of the conveyor, continuously monitoring the laser system to determine when the next plurality of pulses will be produced, directing the next available plurality of pulses to irradiate an identified scrap particle, wherein the selected time interval of the pulses allows each of the plurality of pulses to strike the particle without re-directing the laser pulses, analyzing signals provided from at least one of the selected bands of the collected light thereafter received from the target location by employing a neural network to perform at least part of the analysis, and selectively activating the separator based on the results of the analysis to sort the scrap particles.

* * * * *